United States Patent [19]

Tocker

[11] Patent Number: 4,820,336

[45] Date of Patent: Apr. 11, 1989

[54] HERBICIDAL SPRAY MIXTURES

[75] Inventor: Stanley Tocker, Wilmington, Del.

[73] Assignee: E. I. Du Pont de Nemours and Company, Wilmington, Del.

[21] Appl. No.: 1,335

[22] Filed: Jan. 7, 1987

Related U.S. Application Data

[63] Continuation-in-part of Ser. No. 741,625, Jun. 5, 1985, abandoned.

[51] Int. Cl.$^4$ .................... A01N 43/707; A01N 33/06
[52] U.S. Cl. ............................................. 71/93; 71/121
[58] Field of Search ............................................. 71/93

[56] References Cited

U.S. PATENT DOCUMENTS

| | | | |
|---|---|---|---|
| 3,671,523 | 6/1972 | Westphal et al. | 71/93 |
| 3,847,914 | 11/1974 | Dickore et al. | 71/93 |
| 3,905,801 | 9/1975 | Fawzi | 71/93 |
| 3,920,442 | 11/1975 | Albert et al. | 71/93 |
| 4,150,968 | 4/1979 | Young et al. | 71/93 |
| 4,457,774 | 7/1984 | Eue et al. | 71/93 |

OTHER PUBLICATIONS

Hack et al., "SMY 1500—A New Selective Herbicide for Weed Control in Winter Cereals", Brit. Crop Protect. Confer., 1985, pp. 35–42.

Chem. Abst., vol. 104: 124,920k, Hack et al., "SMY 1500 Selective Herbicide . . . ".

Chem. Abst., vol. 93: 20,638n, Pintilie et al., " . . . Integrated Weed Control . . . ".

*Primary Examiner*—Glennon H. Hollrah
*Assistant Examiner*—Susan P. Treanor

[57] ABSTRACT

The use of selected metribuzin analogs to control crystallization of metribuzin in mixtures of metribuzin and aromatic hydrocarbon-based grass killing herbicides is disclosed.

7 Claims, No Drawings

HERBICIDAL SPRAY MIXTURES

BACKGROUND OF THE INVENTION

It is customary to formulate herbicides as water-dispersable compositions which can be mixed readily with water and applied by means of spraying apparatus. An important class of herbicides which can be applied by this means comprises the asymmetrical N-amino triazines, of which 4-amino-6-(1,1-dimethylethyl)-3-(methylthio)-1,2,4-triazin-5(4H)-one (metribuzin) is used widely. Agriculturally useful formulations of this herbicide are marketed throughout the world under the trademark Lexone ® weed-killing compounds (trademark of E. I. du Pont de Nemours and Company, Wilmington, Del.) or Sencor ® (trademark of Mobay Chemical Company, Kansas City, Mo.).

Metribuzin is employed commonly for selective control of broadleaf weeds in crops such as soybeans. To improve the spectrum of weed control, commercially available formulations of metribuzin (such as Lexone ® 50WP, Lexone ® 4L, Lexone ® 75DF, Sencor ® 50WP and Sencor ® 4F ) are combined commonly in spray tanks with grass-killing herbicides. The grass-killing herbicides often are formulated as aromatic hydrocarbon-based emulsifiable concentrates. Representative examples of grass-killing herbicides which can be combined with metribuzin are Treflan ® (trademark of Elanco Products Company, Indianapolis, Ind., for a trifluralin formulation), Prowl ® (trademark of American Cyanamid Co., Bound Brook, N.J., for a penoxalin formulation), Basalin ® (trademark of BASF Wyandotte Corp., Parsippany, N.J., for a fluchloralin formulation), and Tolban ® (trademark of Ciba-Geigy Corp., Greensboro, N.C., for a profluralin formulation). When applied in the field, these mixtures are diluted in spraytanks with water or liquid fertilizer to form spray mixtures.

Suspensions of metribuzin in water can be utilized without difficulty. When a solution of grass herbicide in an aromatic hydrocarbon solvent is added to the metribuzin/water suspension, however, significant growth and settling of metribuzin crystals can occur. Variation of the grass herbicide and its associated aromatic hydrocarbon solvent results in differing rates and extent of crystallization with the greatest problem observed when the solubility of metribuzin in the hydrocarbon solvent is high. This crystal growth is observed especially in those instances when the spray mixture is allowed to stand unagitated for periods of twelve hours or more. Such situations are not uncommon, occurring, for example, when rain or darkness delays completion of spraying in the field.

The crystallization of metribuzin within the spray apparatus can result in the plugging of field-sprayer spray nozzles. This is most likely to occur when a crystal size of about 50μ, or larger, is reached in any dimension. Plugging of spray nozzles is a significant economic detriment for the reasons that (1) manpower time must be expended to discontinue spraying operations and remove the plugging material and (2) any area sprayed before the plugging is detected and corrected is likely to have been covered improperly. Thus, there is a considerable practical need for a means of controlling metribuzin crystal growth in these spraytank combinations.

SUMMARY OF THE INVENTION

This need is met by the present invention which, in its first aspect, is a composition for mixing with an aromatic hydrocarbon-based, emulsifiable, grasskilling herbicide formulation in an aqueous medium, the composition consisting essentially of metribuzin and a compound of the formula

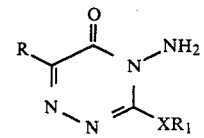

wherein
X is S or $NR_2$;
R is $C_1$–$C_4$ alkyl;
$R_1$ is $C_1$–$C_4$ alkyl;
$R_2$ is H or $C_1$–$C_4$ alkyl;
provided that:
when $R_1$ is $CH_3$ and X is S, then R is other than tertiary butyl.

In its second aspect, the present invention is an improvement in a method for controlling unwanted vegetation, which method comprises (1) combining (a) an agriculturally useful formulation comprising metribuzin, and (b) an aromatic hydrocarbon-based, emulsifiable, grass-killing herbicide formulation in an aqueous medium to produce a formulation mixture which is subject to unwanted crystallization of metribuzin; and (2) spraying the formulation mixture onto a locus on which the control of unwanted vegetation is desired, the improvement comprising:

including in the formulation mixture, in an amount effective to retard the rate of metribuzin crystallization, a compound of the formula:

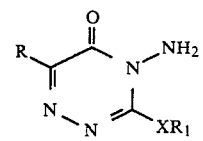

wherein
X is S or $NR_2$;
R is $C_1$–$C_4$ alkyl;
$R_1$ is $C_1$–$C_4$ alkyl;
$R_2$ is H or $C_1$–$C_4$ alkyl;
provided that:
when $R_1$ is $CH_3$ and X is S, then R is other than tertiary butyl.

In its third aspect, the present invention is a process for producing mixtures of metribuzin and compounds of formula I wherein
X is S;
R is tertiary butyl; and
$R_1$ is $C_2$–$C_4$ primary or secondary alkyl, the process comprising treating 4-amino-2,3-dihydro-6-t-butyl-3-thiono-as-triazin-5(4H)-one With a base, a methylating agent and a $C_2$–$C_4$ alkylating agent.

DETAILED DESCRIPTION

The expression "agriculturally useful formulation comprising metribuzin" is meant to denote commercially available metribuzin preparations which comprise metribuzin (generally about 75% by weight) and inert diluents. These preparations are generally in the form of dry, flowable granules and must be diluted with water prior to use. The metribuzin in the formulation is only sparingly soluble in water (0.12 weight percent at 20° C.). Consequently, the bulk of the metribuzin is suspended. Metribuzin formulations within the scope of the present invention are available commercially under the trademarks Lexone ® (E. I. du Pont de Nemours and Company, Wilmington, Del.) and Sencor ® (Mobay Chemical Co., Kansas City, Mo.).

The expression "aromatic, hydrocarbon-based, emulsifiable, grass-killing herbicide formulation" is meant to denote agriculturally useful formulations comprising an active ingredient such as a dinitroaniline herbicide such as trifluralin, fluchloralin, penoxalin, or profluralin, an aromatic hydrocarbon solvent such as xylene, chlorobenzene and heavy aromatic naphtha, and finally some sort of emulsifier.

The presence of the aromatic, hydrocarbon solvent in aqueous mixtures of metribuzin and water is believed to promote the unwanted crystallization problem which the present invention is meant to overcome. Metribuzin is considerably more soluble in aromatic hydrocarbon solvents than it is in water. The presence of the emulsified aromatic hydrocarbon solvent in aqueous suspensions of metribuzin results in crystal growth leading to the formation of crystals of sufficient size to cause the problems mentioned above. Normally a sludge of water, metribuzin crystals, and hydrocarbon material form, over time in the spray tank in which crystal growth of metribuzin occurs. Typical inert diluents in commercial, agriculturally useful formulations of metribuzin can, themselves, retard metribuzin crystallization in the presence of aromatic hydrocarbon solvents, but the problem still remains to such an extent that signIficant clogging of spray nozzles and uneven distribution of metribuzin on crops can occur.

Typical spray suspensions of agriculturally useful formulations comprising metribuzin contain from 0.4 to 4.0 percent of metribuzin based on the weight of the solution. Typical concentrations of aromatic hydrocarbon solvents in aqueous mixtures of metribuzin formulations and aromatic hydrocarbon-based, emulsifiable, grass-killing herbicide formulations are 0.5 to 5.0 percent based on the weight of the mixture. Within these ranges, problematic crystallization occurs, especially when the materials are used at the high end of the concentration ranges.

Crystallization can be quantified by passing the mixture containing the crystals through a screen of controlled pore size and measuring the weight of retained crystals. The efficacy of a crystallization retarding agent such as that contemplated by the present invention can be ascertained by calculating a number known as the "crystallization growth index" (CGI) which is defined as follows:

$$CGI = \frac{W_1 - W_2}{W_1} \times 100\%$$

where $W_1$ = weight of crystals retained on screen when no retardation agent is used: and $W_2$ = weight of crystals retained when retardation agent is used in accordance with the present invention.

For the purposes of quantifying the effects of crystallization retardation in accordance with the present invention, a U S S. 50 mesh screen can be used. This size mesh retains crystals having a size that can cause occlusion of spray nozzles.

To avoid unwanted crystallization of metribuzin in aqueous spray mixtures containing aromatic hydrocarbon solvents, the compound of formula I should be used at a final concentration effective to retard crystallization such that very few crystals large enough to be retained on a U.S.S. 50 mesh screen are present after 24 hours. This effective amount is generally in the range 0.004 to 0.2%. This amount produces a crystal growth index of at least 50 after 24 hours.

In a typical agricultural setting, a dry-flowable metribuzin formulation is suspended in water in a spray tank. A concentrated liquid formulation of an aromatic hydrocarbon-based grass-killing herbicide is added, and the resulting mixture sprayed on crops. The compound of formula I can be added to the mixture as a separate component, but is added most conveniently as a part of the metribuzin formulation.

In accordance with the second aspect of the present invention, metribuzin, at least one compound of formula I, and biologically inert formulation aides are combined to form an agriculturally useful formulation of metribuzin which can be mixed with an aromatic hydrocarbon-based, emulsifiable, grass-killing herbicide without unwanted crystallization. The combination can be granulated to form a dry-flowable substance using well-known procedures. Typically, the weight ratio of the compound of formula I to metribuzin is in the range of 1 to 100, preferably 1 to 15.

Compounds falling within the scope of formula I can be made by the procedures described in U.S. Pat. No. 3,905,801 and U.S. Pat. No. 3,671,523, the disclosures of which are incorporated herein by reference.

In accordance with the third aspect of the invention, a convenient and economical way of simultaneously making metribuzin and those compounds of formula I wherein X is S, R is tertiary butyl and $R_1$ is $C_2$–$C_4$ primary or secondary alkyl is to treat 4-amino-2,3-dihydro-6-t-butyl-3-thiono-as-triazin-5(4H)-one with a base, a methylating agent and a $C_2$–$C_4$ alkylating agent.

$$(CH_3)_3C\text{-triazinone with NH}_2 \xrightarrow[CH_3X]{\text{Base}, R_1X}$$

$$(CH_3)_3C\text{-triazine-SR}_1\text{-NH}_2 \quad +$$

$$(CH_3)_3C\text{-triazine-SCH}_3\text{-NH}_2$$

Suitable bases include alkaline earth hydroxides such as sodium hydroxide or potassium hydroxide.

Suitable methylating agents include methyl bromide or methyl iodide.

Appropriate $C_2$-$C_4$ alkylating agents include ethyl bromide, ethyl iodide or propyl bromide.

The preferred alkylating agents are ethyl iodide or ethyl bromide.

By controlling the ratio of methylating agent to $C_2$-$C_4$ alkylating agent, the relative amounts of metribuzin and the compound of formula I can be controlled. For example where the ratio is 96 to 4 of methyl iodide and ethyl iodide, respectively, the product ratio of $R_1$=methyl to $R_1$=ethyl would be 96 to 4.

Without further elaboration, it is believed that one skilled in the art can, using the preceding description, can use the present invention to its fullest extent. The following preferred specific embodiments are merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A compound within the scope of formula I, 4-amino-6-(1,1-dimethylethyl)-3-(ethylthio)-1,2,4-triazine-5(4H)-one, 1.0 g, referred to hereinafter as 3-ethylthiotriazine, was mixed with 100 g of Lexone ® DF premix powder, a formulation mixture containing 75% metribuzin. This mixture was suspended in a fluidized bed with air pressure and slowly sprayed with 24 mL of water. The resulting suspended granules were dried by heating the air stream from room temperature to 45° C. and were then sieved to isolate the 14–80 mesh fraction. The granules contained 1.3% 3-ethylthiotriazine based on the weight of the metribuzin present. Using the same procedure with 5 g of 3-ethylthiotriazine, granules were prepared containing 6% 3-ethylthiotriazine based on the weight of the metribuzin present.

The granules (2.4 g) (which contained 70–75% metribuzin by weight) were added to 200 mL of water followed by 5 mL of Treflan ® trifluralin herbicide formulation (Elanco Products Co., Indianapolis, Ind.). The mixture was shaken vigorously and allowed to stand at room temperature for 24 hours. The mixture was then passed over a 50 mesh screen which subsequently was washed with water to remove particles smaller than 50 mesh. Solid material remaining on the screen was dried in an air oven at 45° C. and weighed. The results are shown below.

TABLE I

| Percentage 3-ethylthiotriazine in metribuzin granule | Weight of crystals retained on 50 mesh screen |
|---|---|
| 0 | 0.12 g |
| 1.3 | 0.001 g |
| 6 | not measurable |

The data indicate that as little as 1.3% of a compound within the scope of formula I reduces crystallization by almost 100 fold.

EXAMPLE 2

1.2 g Lexone ® DF granules were added to 100 mL water to provide an aqueous suspension of metribuzin. To this suspension was added 1.94 g of xylene (an aromatic hydrocarbon), 0.06 g of 3-ethylthiotriazine (a compound of formula I), 0.19 g Tween ® 40 (an emulsifier) and 0.58 g of technical grade crystalline trifluralin. The mixture was shaken and allowed to stand 24 hours at room temperature. The mixture was passed through a 50 mesh screen. No metribuzin crystals were retained. The experiment was repeated omitting the 3-ethylthiotriazine; over 0.04 g of crystallized metribuzin was retained on the screen. Substitution of toluene for xylene provided similar results.

EXAMPLES 3, 4, and 5

Additional experiments similar to that of Example 1 were conducted to determine the effectiveness of other compounds within the scope of the claimed crystallization suppression compounds of Formula I. These experiments used a hexane premix powder as in control A and involved simple mixtures of the crystallizaton inhibitor of this material. The rate of crystallization of hexane premix powder control (A) and granulated material from it (B) are essentially equivalent. As indicated in Table II, variation of the substituents R and $R_1$ of the crystallization suppression compounds over the widest range possible (R and $R_1$ are butyl to R and $R_1$ are methyl) resulted in effective crystallization suppression during the 24-hour period. The 3-ethylthio analog was most effective.

TABLE II

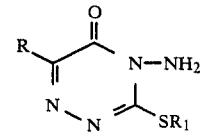

| Experiment | Crystallization Suppressor | Weight of Crystals Retained on 50 mesh Screen |
|---|---|---|
| Control A | None (Lexone ® DF premix powder control) | 0.37 g |
| Control B | None (Lexone ® DF granules control) | 0.38 g |
| C | 3-ethylthiotriazine R = t-butyl $R_1$ = ethyl | Not measurable |
| D | Compound (1) R = t-butyl $R_1$ = n-butyl | 0.09 g |
| E | Compound (2) R = methyl $R_1$ = methyl | 0.11 g |

The extent of crystallization of the controls, as indicated by the amount of crystals retained on the screen, was greater than that shown in Example 1 because of a large difference in temperature during the two sets of experiments. The average room temperature during Experiment 1 was 21°–27° C., whereas in experiments A through E the temperature range was 13°–20° C. The rate of crystallization normally increases as the temperature is reduced.

What is claimed is:

1. In a method for controlling unwanted vegetation, which method comprises:
   (1) combining in an aqueous medium (a) an agriculturally useful formulation coprising metribuzin, and (b) an aromatic hydrocarbon-based, emulsifiable, grass-killing trifluralin herbicide formulation to produce a formulation mixture in which crystal growth of metribuzin occurs over time; and
   (2) spraying the formulation mixture onto a locus on which the control of unwanted vegetation is desired, the improvement comprising;

including in the formulation mixture, in an amount effective to retard the crystal growth of metribuzin, the compound 4-amino-6(1,1 dimethylethyl)-3-(ethyllthio)-1,2,4-triazine-5(4H)-one.

2. The method of claim 1 wherein ethyl metribuzin is included in an amount effective to provide a crystal growth index of greater than 50 after 24 hours as measured using a U.S.S. 50 mesh screen.

3. The process of claim 1 wherein ethyl metribuzin is included in the mixture by inclusion in the formulation of metribuzin.

4. The process of claim 1 wherein the weight ratio of ethyl metribuzin to said metribuzin is from 1 to 15 per 100 parts of metribuzin.

5. The process of claim 4 wherein said weight ratio is from 1.3 to 6% of ethyl metribuzin based on the weight of metribuzin.

6. A crystal growth retardant metribuzin-containing composition for mixing with an aromatic hydrocarbon-based emulsifiable, grass-killing trifluralin herbicide and water and retarding crystal growth of the metribuzin in the resultant suspension over time, consisting essentially of metribuzin and from 1 to 15 parts per 100 parts of metribuzin of the compound 4-amino-6-(1,1-dimethyethyl)-3-(ethylthio)-1,2,4-triazine-5(4H)-one.

7. The composition of claim 1 wherein said weight ratio is from 1.3 to 6% of ethyl metribuzin weight of said metribuzin.

* * * * *